United States Patent [19]

Lauritzen

[11] Patent Number: 5,417,789
[45] Date of Patent: May 23, 1995

[54] ABSORBENT PADS AND PROCESS THEREFOR

[75] Inventor: Nels J. Lauritzen, Piscataway, N.J.

[73] Assignee: McNeil-PPC, Inc., Milltown, N.J.

[21] Appl. No.: 98,009

[22] Filed: Jul. 27, 1993

Related U.S. Application Data

[63] Continuation of Ser. No. 684,629, Apr. 12, 1991, abandoned.

[51] Int. Cl.6 .................. B32B 31/00; A61F 13/15
[52] U.S. Cl. ................... 156/220; 156/324; 156/277; 156/291; 156/275.5; 156/250; 156/244.12; 156/244.16; 156/244.17; 156/244.19; 156/289; 604/358; 604/382; 604/365; 604/375
[58] Field of Search ............... 156/90, 270, 324, 277, 156/273.3, 275.5, 272.2, 244.17, 244.19, 244.11, 244.24, 220, 219, 280, 278, 289, 307.2, 807.1; 604/358, 359, 365, 366, 375, 377, 378, 382, 387

[56] References Cited

U.S. PATENT DOCUMENTS

| | | | |
|---|---|---|---|
| 3,471,428 | 10/1969 | Hodgson | 260/23 |
| 3,616,797 | 11/1971 | Champaigne et al. | 128/290 |
| 3,622,423 | 11/1971 | Hadley | 156/309 |
| 3,688,771 | 9/1972 | Werner | 156/289 X |
| 3,930,890 | 9/1975 | Mesek et al. | 128/287 |
| 3,950,198 | 4/1976 | Cannon et al. | 156/79 |
| 3,976,075 | 8/1976 | Chinai et al. | 604/365 |
| 4,000,028 | 12/1976 | Hoey | 156/289 X |
| 4,035,217 | 7/1977 | Kennette et al. | 156/279 |
| 4,144,371 | 3/1979 | Okie | 428/255 |
| 4,230,521 | 10/1980 | Cobb | 156/324 X |
| 4,324,246 | 4/1982 | Mullane | 128/287 |
| 4,522,863 | 6/1985 | Keck et al. | 428/196 |
| 4,530,353 | 7/1985 | Lauritzen | 128/156 |
| 4,545,372 | 10/1985 | Lauritzen | 128/156 |
| 4,549,653 | 10/1985 | Lauritzen | 206/441 |
| 4,607,633 | 8/1986 | Lauritzen | 128/156 |
| 4,622,089 | 11/1986 | Lauritzen | 156/289 X |
| 4,726,976 | 2/1988 | Karami et al. | 428/137 |
| 4,794,020 | 12/1988 | Lussi et al. | 427/195 |
| 4,847,137 | 7/1989 | Kellen et al. | 156/275.5 X |
| 4,950,500 | 8/1990 | Kauffman et al. | 427/197 |
| 4,976,890 | 12/1990 | Felter et al. | 252/511 |

FOREIGN PATENT DOCUMENTS

| | | |
|---|---|---|
| 0124834A2 | 10/1987 | European Pat. Off. . |
| 1264685 | 3/1968 | Germany . |
| 657615 | 6/1965 | United Kingdom . |
| 1071191 | 6/1967 | United Kingdom . |

OTHER PUBLICATIONS

"Ultraviolet Curing Technology," Techcommentary, vol. 4, No. 4, 1987 (p. 3 of reprint dated Mar., 1990).

*Primary Examiner*—Chester T. Barry

[57] ABSTRACT

A continuous process for manufacturing absorbent pads is disclosed which comprises providing a fibrous web material and applying a fluid absorbent cover and a fluid impermeable barrier layer thereto in situ. In preferred embodiments, the pads are securable to fluid-protected surfaces by means of an adhesive on the barrier layer's outer surface.

27 Claims, 5 Drawing Sheets

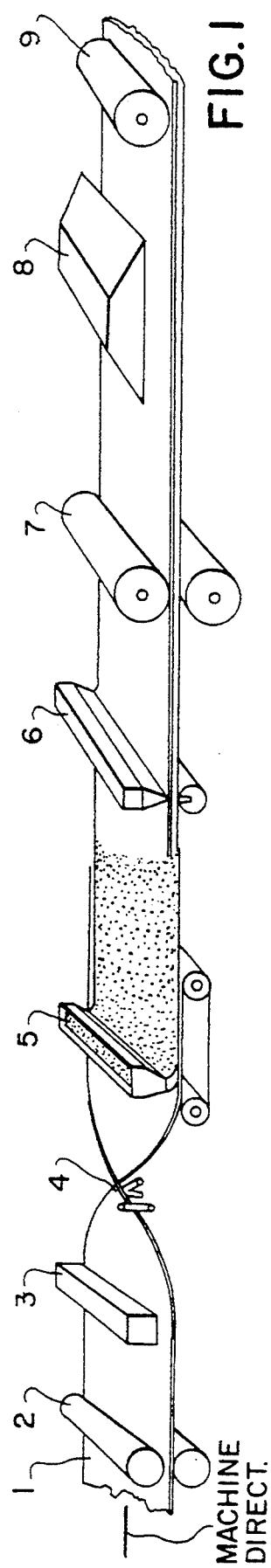

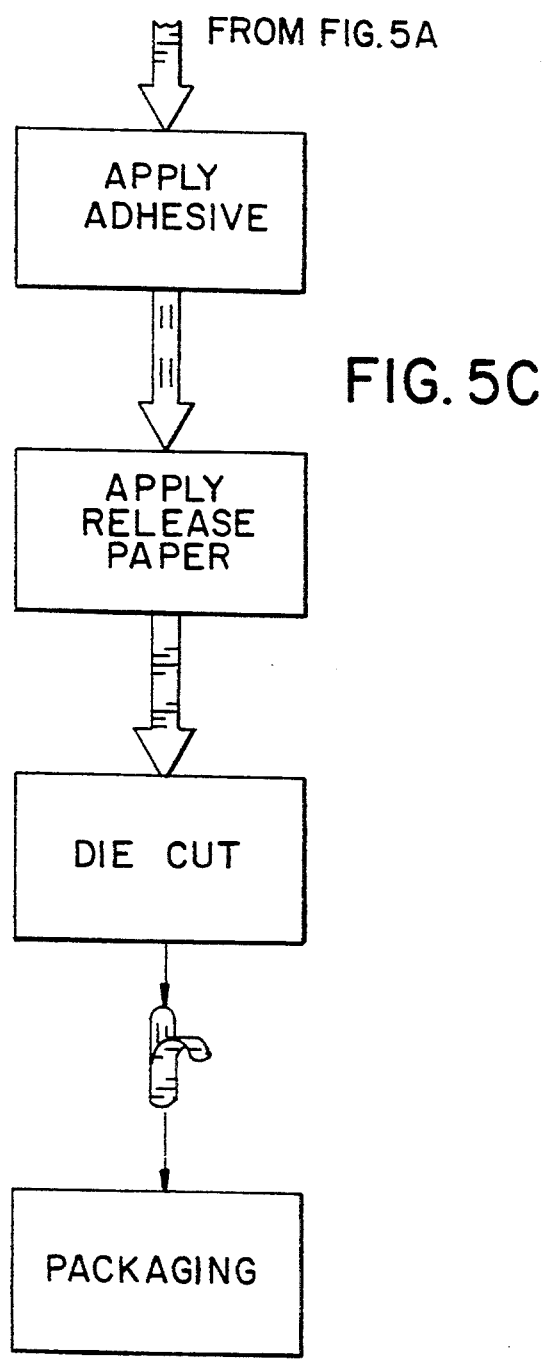

ABSORBENT PADS AND PROCESS THEREFOR

This is a continuation of application Ser. No. 07/684,629, filed Apr. 12, 1991, now abandoned.

BACKGROUND OF THE INVENTION

This invention relates to absorbent pads which adhere to surfaces to be protected from fluid and, more particularly, to a method of manufacturing such absorbent pads through a continuous production technique comprising multiple steps.

Absorbent pads find many common uses, such as in the management of bodily fluids. The utility of such products often derives not only from their absorbent properties but also their ability to prevent the further contact of absorbed fluids with certain surfaces, such as clothing or skin. Such containment is often achieved through the incorporation of a fluid-impermeable barrier layer on one or more surfaces of the absorbent pad. Diapers, bandages, and feminine sanitary napkins provide examples of absorbent pads comprising a fluid-impermeable barrier layer.

In addition to containing and isolating fluids, it is often also desirable for absorbent pads be secured to a particular surface or in a certain position. For example, it is known in the art to secure a sanitary napkin by affixing its barrier layer to a woman's undergarment, typically through the use of adhesives.

Unfortunately, however, the processes traditionally employed in the manufacture of absorbent pads—securable or otherwise—have often involved a series of separate and preliminary raw material processing procedures. Upon completion of such processing, the resultant components must be inventoried and then assembled into a single, integrated product. Such assembly traditionally involves securing various, fully formed components to a pulp core with adhesive. The implementation of multiple, separately processed adhesive-bound raw material components thus typically adds considerable expense and delay to the production of absorbent pads and increases the likelihood of bunching and other forms of pad instability in actual use.

Accordingly, considerable effort has been expended to consolidate the various procedures required in the manufacture of absorbent pads. For example, U.S. Pat. Nos. 4,530,353, 4,545,372, 4,549,653, and 4,607,633, all in the name of Lauritzen, disclose continuous and considerably streamlined production techniques for the manufacture of adhesive bandages and packages therefor. The objects of these patents, however, comprise an absorbent pad area having adjacent adhesive areas and are designed to attach to fluid-bearing surfaces; an item such as a sanitary napkin commonly bears adhesive, if at all, on the surface opposite its absorbent cover and is designed to attach to a surface for which protection from fluid is sought.

It is accordingly an object of the present invention to provide an improved absorbent pad. It is another object of the present invention to provide a low cost absorbent pad through the use of low cost manufacturing techniques. It is a further object of the present invention to provide an absorbent pad having a fluid-impermeable barrier layer. It is still another object of this invention to provide an absorbent pad having both a barrier layer and a means for attachment to a surface to be protected from fluid. It is yet another object of this invention to manufacture such an absorbent pad through a continuous production technique in which all necessary raw material components are incorporated in a stepwise fashion and are bound together in a unitary design not employing adhesives.

SUMMARY OF THE INVENTION

The securable absorbent pads of this invention are produced by a continuous production technique comprising multiple steps. Such pads comprise fibrous web material having a fluid absorbent cover and a fluid impermeable barrier layer applied in Situ to respective surfaces thereof.

The absorbent pads of this invention are prepared from low cost, stabilized, fibrous web material. The fluid permeable and fluid-impermeable barrier layer are ultimately attached to opposite surfaces of this web material. The barrier layer may be applied either before or after application of the cover; it is preferred, however, that the barrier layer be applied after the cover.

A preferred means of applying the absorbent cover is to draw the fibrous web material substrate through a rotary screen printing station at which the cover is pattern-applied, as is well known in the art. Film forming polymer can be applied to the web's surface, impregnated into the web, or imprinted through top and bottom web surfaces. In preferred embodiments of this invention, a rotary screen applies a relatively heavy (0.4–1.2 ounces/yard) amount of a cover formulation to an upwardly exposed side of the fibrous web material. The particular pattern in which the cover is applied is chosen such that it is aesthetically pleasing, facilitates proper placement of the pad, or is effective in providing surface channels and reservoirs to aid in fluid management.

Preferably, the cover formulation comprises a plastisol. As known to those of skill in the art, a plastisol is a vinyl resin dispersed in a plasticizer to yield a pourable liquid suitable for casting. Plastisol employed in the practice of this invention can be foamed or unfoamed. As known to those of skill in the art, the use of plastisol foam increases the cover's working surface and forms surface channels which encourage vertical fluid penetration into the pad.

Preferably, cover formulations used in the present invention should comprise about 100% of polyvinylchloride with plasticizers. The cover formulation preferably also comprises other active ingredients, such as surfactants. A particular plastisol formulation is chosen to provide surfactants readily to the cover surface and to impart to the cover good appearance, and fluid management. Plastisol may provide same odor control activity as well.

After application, the cover is cured to improve the structural integrity of its pattern. Curing can be carried out in many ways such as radiant energy, ultrasonic or mechanical energy, or ultraviolet energy. Exposure to infrared radiation is a preferred curing technique.

As will be appreciated by those of skill in the art, there exist numerous techniques by which various types of fluid-impermeable barrier layers might be applied to the absorbent pads of this invention. Preferably, the barrier layer is applied to an upwardly exposed surface of the fibrous web material. A preferred means of barrier layer application is direct extrusion of a suitable compound onto the exposed surface of the fibrous web material. Preferably, the compound should have hydrophobic properties; a preferred hydrophobic compound is polyethylene or the like. The fibrous web material and the extruded barrier must be chosen so as to be compatible. This will ensure adequate barrier layer anchorage.

Once the barrier layer has been applied to the fibrous web, a texture may optionally be imparted to the barrier layer by means well known to those of skill in the art, such as the application of embossed or etched chill roll immediately after extrusion. Indeed, such texture is preferred on the barrier layer to reduce plastic "noise" and "feel".

In accordance with this invention, adhesive is next applied in a controlled pattern to the surface of the barrier layer. Rotary and screen type roll print processes provide a preferred means of adhesive application, although there are other types of adhesive application known to those of skill in the art. In a preferred embodiment of this invention, the adhesive employed is a hot melt adhesive capable of being cured and cross-linked; it is especially preferred that the adhesive cure upon exposure to radiation energy. In some preferred embodiments, release paper is applied directly over the adhesive to prevent subsequent, undesired attachment of the absorbent pad. However, in some embodiments, release paper may not be necessary.

The resultant work product may then be cut into any number of shapes and sizes to yield securable absorbent pads as required for specific applications. Using a die cutting station, for example, many complicated product variations are possible while maintaining high production rates; such variations are effected by varying the nesting design employed at the die cutting station.

Additional processing steps can optionally be included at various stages in the production of the absorbent pads of this invention. For example, active ingredients such as "super-absorbents" and odor control agents can be applied as dry powders to the surface of either the fibrous web material, barrier layer, or cured absorbent cover. Alternatively, the active ingredients may be added between the barrier and web material during extrusion.

BRIEF DESCRIPTION OF THE DRAWINGS

FIG. 1 is a schematic representation in perspective of one embodiment of the present invention, illustrating a continuous, sequential technique for the production of securable absorbent pads.

FIGS. 2A, 2B, 2C are top plan views of absorbent cover pattern designs employable in embodiments of the present invention.

FIGS. 3A, 3B, 3C are top plan views of nesting designs employable in embodiments of the present invention.

FIGS. 4 and 5A, 5B and 5C represent two embodiments of processes according to this invention.

DESCRIPTION OF A PREFERRED EMBODIMENT

Figure 4:
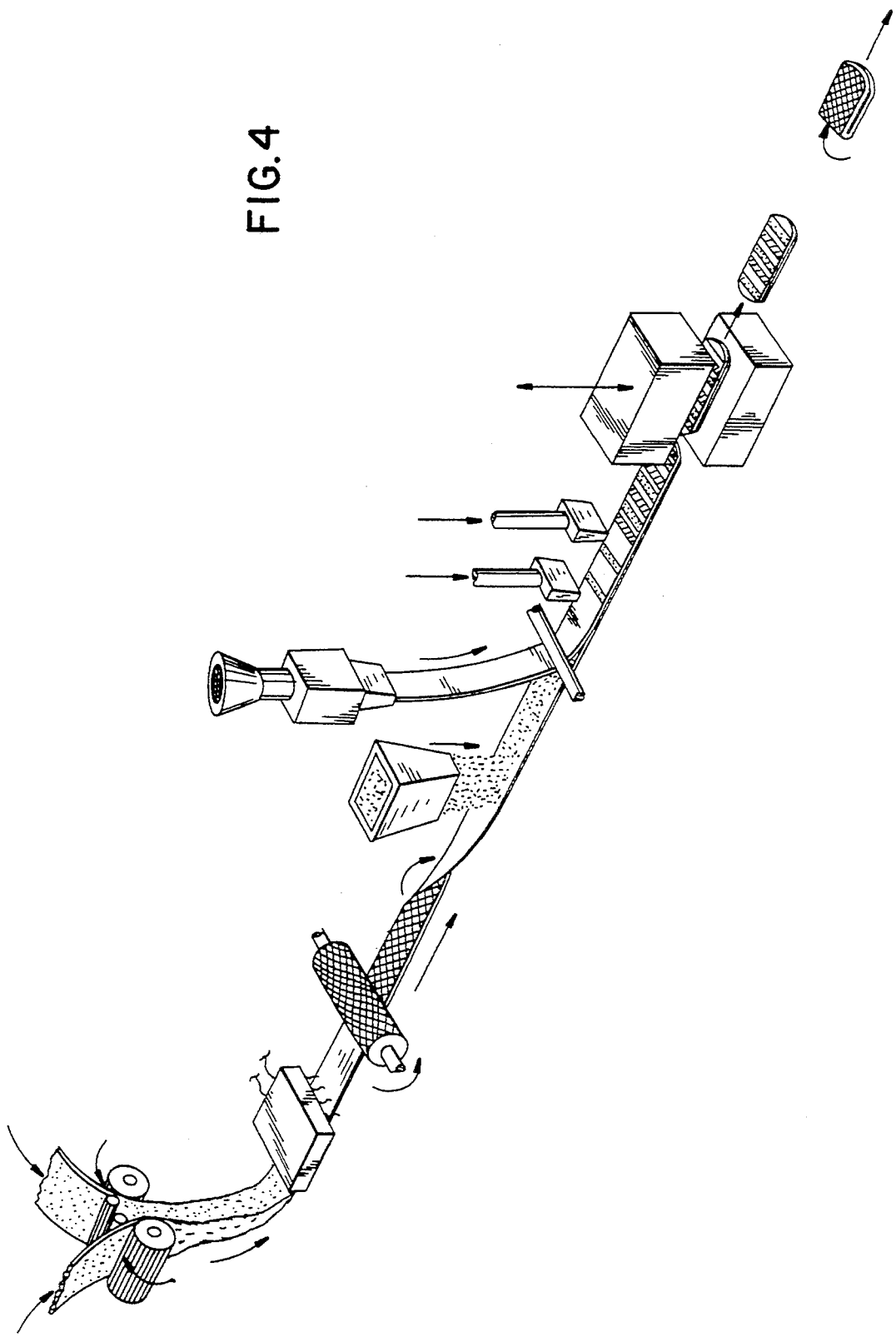

The present invention provides a continuous process for manufacturing absorbent pads having a fluid absorbent cover and a fluid impermeable barrier layer formed in situ. In particular, a preferred process provides feminine sanitary napkins securable to the central crotch portion of an undergarment. These products further comprise an adhesive on the outer surface of said barrier layer.

As seen in FIG. 1, a fibrous web material (1) such as Scotts High Loft SPP is brought through a rotary screen printing station (2). A thermally stabilized web which is made up of various blends containing thermoplastic fibers such as Enka bicomponent fiber having a polyester core and a polyethyene sheath, and Dupont Pulplus ®, a polyethylene microfiber available from E. I. dupont de Nemours, Wilmington, Del., may be used. At printing station (2), a foamed or unfoamed plastisol cover formulation is pattern applied, using one of the patterns given in FIG. 2. Design 2a is chosen to be aesthetically pleasing, design 2b to assist in pad placement, and design 2c to aid in fluid management. The rotary screen is used to apply between 0.4 and 1.2 ounces/yard of a plastisol cover formulation containing 50% by weight polyvinyl chloride resin, such as Geon ® 180×5 available from B. F. Goodrich and 50% plasticizer is such as butyl benzyl phthalate. One such plasticizer, is Santicizer 160, available from Monsanto.

In addition, other ingredients may be included in the general formula for specific characteristics. For example, titanium dioxide may be added as a whitening agent. Silicone may be added as a hydrophilic finish.

The plastisol cover is then heat cured as it passes through an infrared tunnel (3) in which its temperature is brought to 350–450 degrees Fahrenheit for between 15–45 seconds.

The web material with cover is then turned over (4) in order to begin working on what will become the product's barrier layer. In preferred embodiments, a dry powder formulation comprising odor control agents or superabsorbents is applied at this point (5) to the exposed web material. Encapsulated materials may also be so applied.

The barrier layer is next applied by direct extrusion onto the fibrous web. The extruder (6) delivers a hydrophobic barrier of polyethylene directly to the treated surface of the web material.

Location adhesive is then applied through a rotary roll print process (7) which distributes the adhesive in a controlled pattern. The printed hot melt adhesive is then cross-linked and cured as it passes through an ultraviolet curing unit (8), after which release paper is applied directly over the cured adhesive.

Web material having both an absorbent cover and a fluid impermeable barrier layer is next cut into securable absorbent pads at a die cutting station (9). Preferred nesting designs at the die cutting station are given in FIG. 3.

Figure 5A:
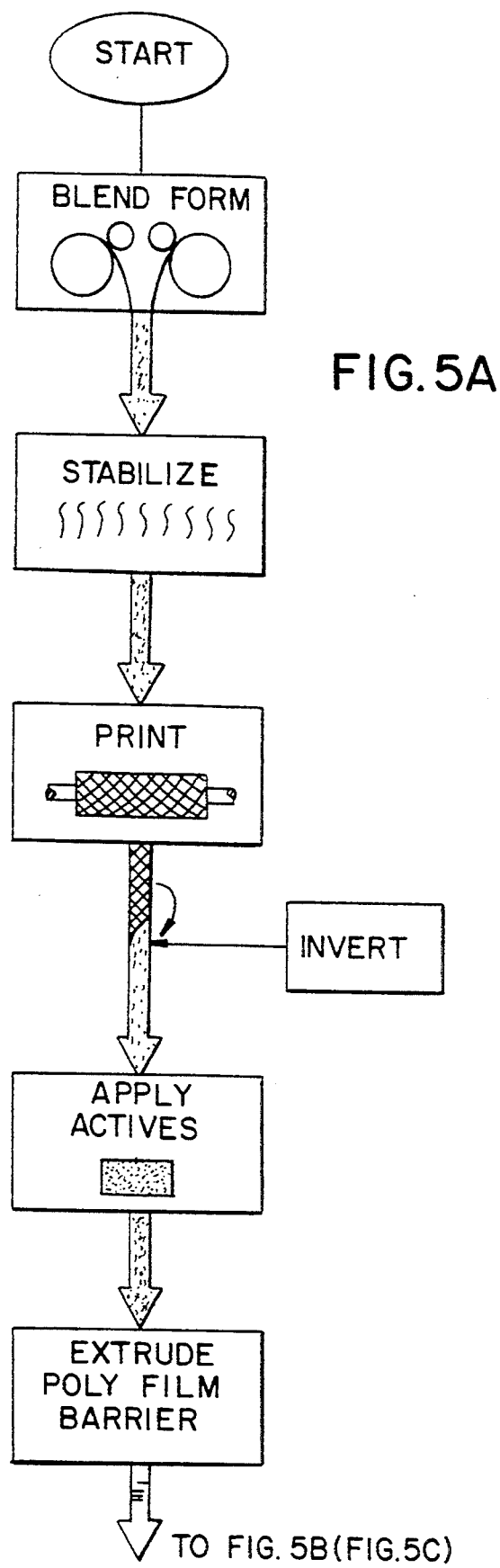
Figure 5B:
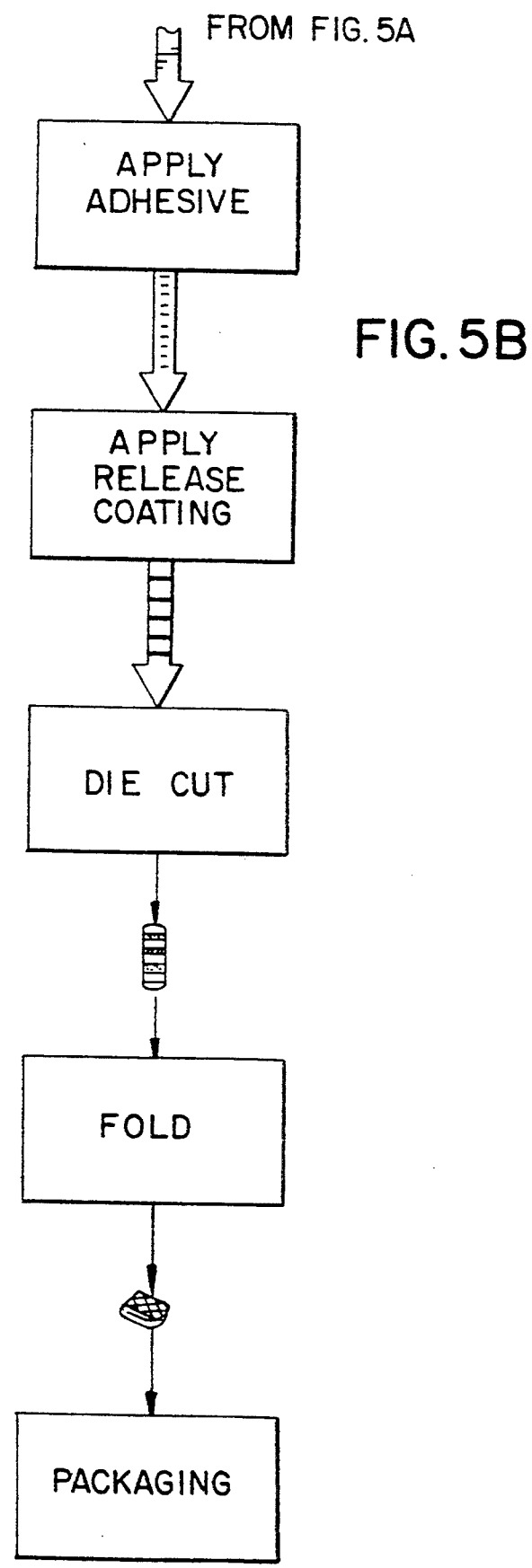

FIGS. 4 and 5A, 5B and 5C illustrate variations of the process embodiment depicted in FIG. 1. Thermoplastic fusible fiber, e.g. Enka bicomponent fiber, DuPont Pulplus ®, and pulp, are blended and a nonwoven web is formed (1). The web is stabilized (2) by exposure to infrared energy. A plastisol composition containing polyvinyl chloride, a plasticizer and a foaming agent such as nitrogen which "out-gases" during the curing step is printed (3) onto the nonwoven web and the web, having been printed, is continuously inverted (4). A powder active, such as sodium bicarnbonate or another active odor control material, is applied to the inverted web (5) by shaking. A barrier material, such as low density polyethylene film, is extruded onto the web (6). At this juncture, the coated web may be directed to one of two process lines: either the web may be coated with adhesive by extrusion or spraying (7a), release paper applied (8a), die-cut (9a) and packaged (10a) or it may be die-cut (7b), adhesive applied (9b) and packaged (10b) without release paper.

What is claimed is:

1. A method of manufacturing a plurality of absorbent pads, each of which is comprised of a plurality of components, in a continuous production process wherein at least a portion of said components are formed in situ, comprising the steps of:
   providing a continuous length of fibrous web material having at least first and second surfaces, said continuous length of fibrous web material being sufficiently long to form a plurality of said absorbent pads;
   continuously printing a film forming polymer onto said first surface of said fibrous web material in a pattern having open areas and so as to form and bond a fluid permeable cover having fluid directing channels and fluid retaining reservoirs directly onto said first surface of said fibrous web material and so as to bond said cover to said fibrous web material without the use of adhesives;
   continuously curing said fluid permeable cover after said cover has been applied to said fibrous web material;
   continuously forming and immediately thereafter applying a fluid impermeable barrier layer directly upon said second surface of said fibrous web material so as to bond said barrier layer to said fibrous web material without the use of adhesives; and
   repeatedly cutting said fibrous web material having said absorbent cover and barrier layer applied thereto so as to form a plurality of absorbent pads.

2. The method of claim 1 wherein said fluid permeable cover is pattern applied.

3. The method of claim 1 wherein said fluid permeable cover comprises plastisol.

4. The method of claim 1 wherein said fluid permeable cover consists essentially of about 100 weight percent plastisol.

5. The method of claim 1 wherein said fluid permeable cover comprises odor control agents.

6. The method of claim 1 wherein said fluid permeable cover comprises surfactants.

7. The method of claim 1 wherein said fluid permeable cover is cured with radiant energy.

8. The method of claim 7 wherein said radiant energy is infrared radiation.

9. The method of claim 1 wherein said barrier layer is formed and applied to said fibrous web material by directly extruding a hydrophobic compound onto said second surface of said fibrous web.

10. The method of claim 1 wherein said barrier layer comprises polyethylene.

11. The method of claim 1 further comprising the step of imparting texture to said barrier layer.

12. The method of claim 1 further comprising the step of continuously applying adhesive in a pattern upon said barrier layer after the step of applying said barrier layer to said fibrous web material and prior to the step of cutting said fibrous web material.

13. The method of claim 12 further comprising the step of applying release paper over said adhesive.

14. The method of claim 12 wherein said adhesive is applied by a roll print process.

15. The method of claim 12 wherein said adhesive comprises a hot melt adhesive.

16. The method of claim 12 further comprising the step of curing said adhesive.

17. The method of claim 16 wherein said adhesive is cured with ultraviolet radiation.

18. The method of claim i further comprising the steps of:
   orienting said fibrous web material so that said first surface faces upward and said second surface faces downward prior to said application of said fluid permeable cover; and
   inverting said fibrous web material so that said second surface faces upward and said first surface faces downward prior to said application of said barrier layer.

19. The method of claim i wherein the step of providing a fibrous web material comprises the steps of:
   continuously blending hi-component fibers and pulp in situ to form a non-woven web; and
   continuously stabilizing said non-woven web and then immediately thereafter applying said fluid impermeable cover.

20. The method of claim 1 wherein said film forming polymer comprises a plastisol compound containing a surfactant.

21. The method of claim 1 wherein said film forming polymer comprises a plastisol compound containing a foaming agent.

22. The method of claim 1 wherein said film forming polymer comprises a plastisol compound containing a whitening agent.

23. The method of claim 1 wherein said film forming polymer is applied with a rotary screen.

24. The method of claim 1 wherein said film forming polymer is applied in an amount of 0.4 to 1.2 ounces per yard.

25. A method of manufacturing a plurality of absorbent pads in a continuous production process, comprising the steps of:
   providing a continuous length of fibrous web material having at least first and second surfaces, said continuous length of fibrous web material being sufficiently long to form a plurality of said absorbent pads;
   continuously forming in situ a fluid permeable cover and continuously applying said fluid permeable cover thus formed to said first surface of said fibrous web material;
   continuously curing said fluid permeable cover after said cover has been applied to said fibrous web material;
   continuously and directly extruding a fluid impermeable barrier layer in situ onto said second surface of said fibrous web material; and
   repeatedly cutting said fibrous web material having absorbent cover and barrier layer applied thereto so as to form a plurality of absorbent pads.

26. An absorbent pad produced in accordance with claim 1.

27. An absorbent pad produced in accordance with claim 12.

* * * * *

UNITED STATES PATENT AND TRADEMARK OFFICE
CERTIFICATE OF CORRECTION

PATENT NO.　：　5,417,789
DATED　　　：　May 23, 1995
INVENTOR(S)：　Nels J. Lauritzen

It is certified that error appears in the above-indentified patent and that said Letters Patent is hereby corrected as shown below:

Column 6 - Line 8  -  "i" should be "l"

Line 17 -  "i" should be "l"

Signed and Sealed this

Fifth Day of September, 1995

Attest:

BRUCE LEHMAN

*Attesting Officer*　　　*Commissioner of Patents and Trademarks*